US011676726B2

(12) United States Patent
Haase

(10) Patent No.: US 11,676,726 B2
(45) Date of Patent: Jun. 13, 2023

(54) APPARATUS AND METHOD FOR GENERATING A TREATMENT PLAN FOR SALUTOGENESIS

(71) Applicant: David Haase, Brentwood, TN (US)

(72) Inventor: David Haase, Brentwood, TN (US)

(73) Assignee: David Haase, Brentwood, TN (US)

( * ) Notice: Subject to any disclaimer, the term of this patent is extended or adjusted under 35 U.S.C. 154(b) by 0 days.

(21) Appl. No.: 17/846,191

(22) Filed: Jun. 22, 2022

(65) Prior Publication Data

US 2022/0406462 A1 Dec. 22, 2022

Related U.S. Application Data

(60) Provisional application No. 63/213,263, filed on Jun. 22, 2021.

(51) Int. Cl.
*G16H 50/20* (2018.01)
*G06N 20/00* (2019.01)
*G16B 40/00* (2019.01)

(52) U.S. Cl.
CPC ............. *G16H 50/20* (2018.01); *G06N 20/00* (2019.01); *G16B 40/00* (2019.02)

(58) Field of Classification Search
CPC ......... G16H 50/20; G06N 20/00; G16B 40/00
See application file for complete search history.

(56) References Cited

U.S. PATENT DOCUMENTS

| 11,357,444 | B1* | 6/2022 | McNair | G06N 5/01 |
| 2012/0269420 | A1* | 10/2012 | Najarian | A61B 5/412 |
| | | | | 382/134 |
| 2017/0269095 | A1* | 9/2017 | Lee | A61K 49/0093 |
| 2018/0000972 | A1* | 1/2018 | Lee | G01N 33/6893 |
| 2018/0128839 | A1* | 5/2018 | Ochsner | G01N 33/6893 |
| 2019/0221316 | A1* | 7/2019 | Goebel | G06F 17/15 |
| 2020/0310098 | A1* | 10/2020 | Ince | G06T 7/0012 |
| 2022/0142947 | A1* | 5/2022 | Friedman | A61K 9/0014 |
| 2022/0157470 | A1* | 5/2022 | Sylvestre | G16H 50/20 |

\* cited by examiner

*Primary Examiner* — Jay M. Patel
(74) *Attorney, Agent, or Firm* — Caldwell Intellectual Property Law

(57) ABSTRACT

An apparatus and method for generating a treatment plan for salutogenesis, the apparatus comprising a at least a processor and a memory communicatively connected to the processor, the memory containing instructions configuring the at least a processor to receive physiological data associated with a user and comprising a plurality of biomarkers, wherein the plurality of biomarkers comprise at least a glycocalyx degradation biomarker, determine a concentration for each at least a glycocalyx degradation biomarker of the plurality of biomarkers, classify the at least a glycocalyx degradation biomarker to a disease condition and a treatment label as a function of the concentration, and generate a treatment plan as a function of the disease condition and the treatment label.

20 Claims, 7 Drawing Sheets

…

APPARATUS AND METHOD FOR GENERATING A TREATMENT PLAN FOR SALUTOGENESIS

CROSS-REFERENCE TO RELATED APPLICATIONS

This application claims the benefit of priority of U.S. Provisional Patent Application Ser. No. 63/213,263, filed on Jun. 22, 2021, and titled "SYSTEMS AND METHODS FOR GENERATING A TREATMENT PLAN," which is incorporated by reference herein in its entirety.

FIELD OF THE INVENTION

The present invention generally relates to the field of medicine. In particular, the present invention is directed to apparatus and method for generating a treatment plan for salutogenesis.

BACKGROUND

Replacement therapy is widely used to treat many ailments. Most common uses for replacement therapy are the replacing a lost nutrient or substance. For example, hormone replacement therapy is primarily used to treat menopausal effects or osteoporosis by treatment with estrogens or progestogens. Other types of replacement therapies aim at epidermal hydration, skin elasticity, skin thickness, and also reduces skin wrinkles. Implementing such therapies to treat major ailments can be challenging.

SUMMARY OF THE DISCLOSURE

In one aspect of the disclosure, an apparatus for generating a treatment plan for salutogenesis is shown. The apparatus comprises at least a processor and a memory communicatively connected to the processor, the memory containing instructions configuring the at least a processor to receive physiological data associated with a user and comprising a plurality of biomarkers, determine a concentration for each biomarker of the plurality of biomarkers, classify each biomarker to a disease condition and a treatment label as a function of the concentration, wherein the classification further comprises receiving treatment training data correlating each biomarker and its concentration with the disease condition and the treatment label and training a treatment classifier using the treatment training data, classifying each biomarker to the disease condition and the treatment label using the treatment classifier, and generate a treatment plan as a function of the disease condition and the treatment label.

In another aspect of the disclosure, a method for generating a treatment plan for salutogenesis is presented. The method comprising receiving, at a processor, physiological data associated with a user and comprising a plurality of biomarkers, determining, at a processor, a concentration for each biomarker of the plurality of biomarkers, classifying, at a processor, each biomarker to a disease condition and a treatment label as a function of the concentration, wherein the classification further comprises receiving treatment training data correlating each biomarker and its concentration with the disease condition and the treatment label, training a treatment classifier using the treatment training data, and classifying, at a processor, each biomarker to the disease condition and the treatment label using the treatment classifier, and generating, at a processor, a treatment plan as a function of the disease condition and the treatment label.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and method for generating a treatment plan for salutogenesis. The system includes at least a processor and a memory communicatively connected to the processor wherein the memory containing instructions configuring the at least a processor to perform steps. At least a processor may receive physiological data associated with a user and comprising a plurality of biomarkers. The apparatus determines a concentration for each biomarker of the plurality of biomarkers. The apparatus also classifies each biomarker to a disease condition and a treatment label as a function of the concentration. The classification further comprises receiving treatment training data correlating each biomarker and its concentration with the disease condition and the treatment label and training a treatment classifier using the treatment training data. The apparatus then generates a treatment plan as a function of the disease condition and the treatment label.

Figure 1:
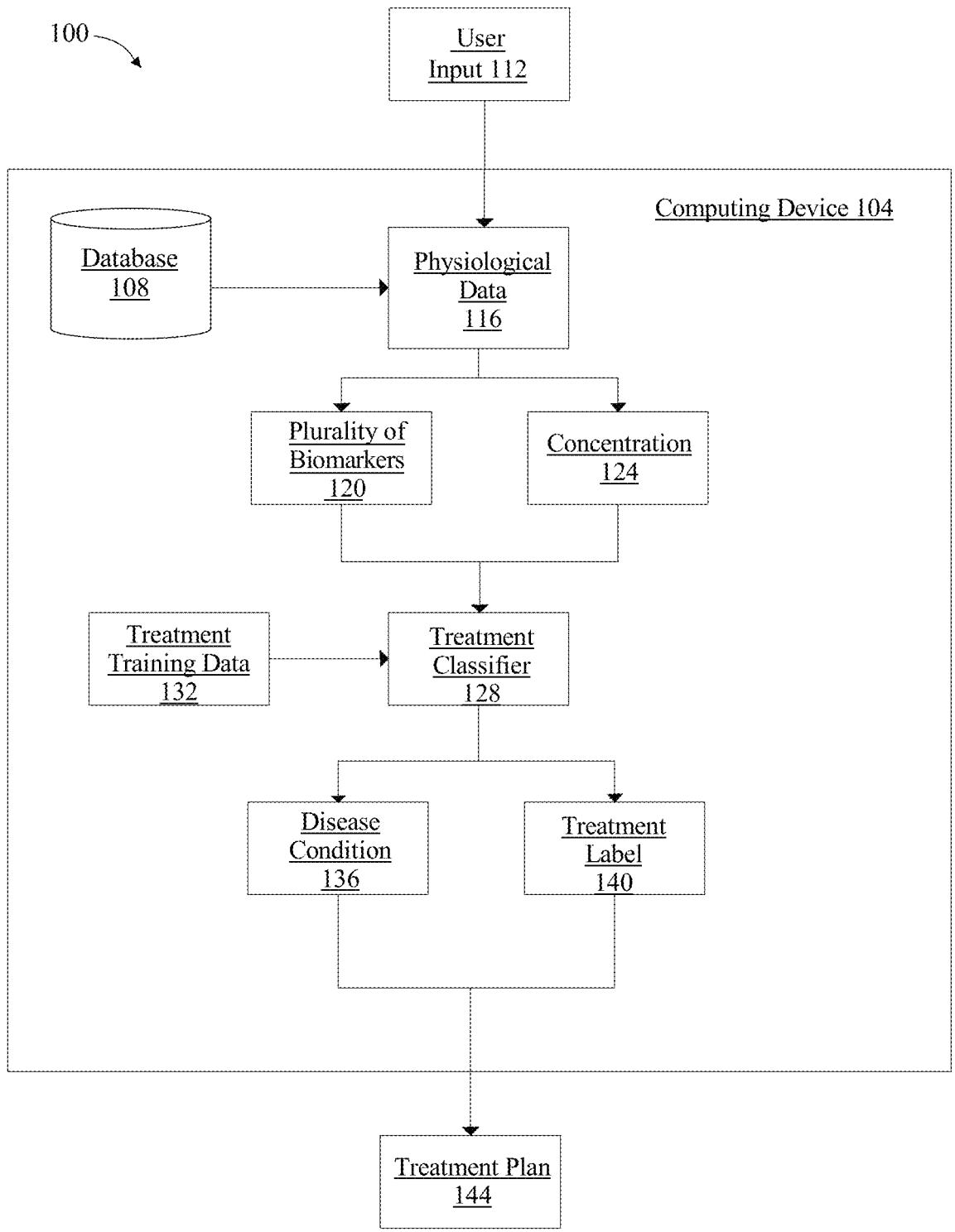
FIG. 1 is a block diagram of an exemplary embodiment of an apparatus for generating a treatment plan for salutogenesis.

Now referring to FIG. 1, an exemplary embodiment of a block diagram of an apparatus for generating a treatment plan for salutogenesis is illustrated. Apparatus 100 comprises at least a processor and a memory communicatively connected to the processor, the memory containing instructions configuring the at least a processor to perform steps as described herein. At least a processor may be a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive physiological data 116 associated with a user. As used in this disclosure, "physiological data" is data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological data 116 may include, but not limited to any medical test, a user's health assessment, a user's medical history, an assessment conducted in any website providing information related to a medical condition, a direct entry from a user, and the like. As a non-limiting example, and without limitation, physiological data 116 describing red blood cells may be recognized as useful for identifying various conditions such as dehydration, high testosterone, nutrient deficiencies, kidney dysfunction, chronic inflammation, anemia, and/or blood loss. For instance, and without limitation, a particular set of biomarkers, test results, and/or biochemical information may be recognized in each medical field as useful for identifying various disease conditions or prognoses within a relevant field.

In an embodiment, physiological data includes a plurality of biomarkers 120. A "biomarker", as used in this disclosure, is a biological and/or chemical substance or process that is indicative of a particular functioning in the body. Plurality of biomarkers 120 may include, without limitation, red blood cell count, hemoglobin levels, hematocrit, mean corpuscular volume, mean corpuscular hemoglobin, and/or mean corpuscular hemoglobin concentration. Plurality of biomarkers 120 may comprise at least a glycocalyx degradation biomarker, which is further explained below. The presence of at least one biomarker may indicate a likelihood that a user is currently experiencing or might experience some disease at a future date. For instance, early detection of tumor necrosis factor-alpha (TNF) from the TNF cytokine family which triggers many intracellular processes may indicate that the user may be experiencing or will experience symptoms of, rheumatoid arthritis, for example. Plurality of biomarkers 120 may include, for example, monitoring biomarkers. A "monitoring biomarker," as used in this specification, is a biomarker that may be used to assess the progress of a disease or to monitor the effects of a therapeutic agent, such as, for example, administration of a course of antibiotics. In another example, a biomarker may be a diagnostic biomarker. A "diagnostic biomarker," as defined in this disclosure is a biomarker that is used to detect the presence of a disease or a condition of interest. Another example of a biomarker is a predictive biomarker. A "predictive biomarker," as used in this disclosure, is a biomarker used to predict what group of patients will respond favorably or unfavorably to a particular treatment. In an embodiment, plurality of biomarkers 120 may include a predictive biomarker. Examples of plurality of biomarkers 120 that may be used in diagnosing a, for instance, type-2 diabetes may include branched chain amino acids (BCAA) which may be associated with hyperglycemia and may be a predictive biomarker for type-2 diabetes. Other potential predictive biomarkers of diabetes risk include dimethylglycine (DMG), 2-amino adipic acid, and glycine. Plurality of biomarkers 120 may be extracted, for example, chemically. For instance, an enzyme-linked immunosorbent assay ("ELISA") may be used to identify at least one disease biomarker. For instance, the presence of Interleukin IL-1β (IL-1β) and/or matrix metalloproteinase (MMP-9) may indicate the potential for the presence of a renal disease. Plurality of biomarkers 120 may be extracted, for example, from a research journal. Alternatively, plurality of biomarkers 120 may be extracted by experimentation. For example, a biomarker that may indicate a particular disease may incorporate testing for the presence of a biomarker using a control group where the group does not have the biomarker present. Values for the biomarker for a sample group known to have the biomarker present may be compared against the values obtained for the control group and a determination made regarding the presence of a particular disease.

Additionally or alternatively, with continued reference to FIG. 1, plurality of biomarkers 120 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Plurality of biomarkers 120 may include, without limitation, immune function data such as Interleukine-6 (IL-6), TNF-alpha, systemic inflammatory cytokines, and the like.

Continuing to refer to FIG. 1, plurality of biomarkers 120 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Plurality of biomarkers 120 may include measures of glucose metabolism such as fasting glucose levels and/or hemoglobin A1-C (HbA1c) levels. User input may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Plurality of biomarkers 120 may include measures of estimated glomerular filtration rate (eGFR). Plurality of biomarkers 120 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Plurality of biomarkers 120 may include peptides, lipid analysis, growth factors, micro-RNA, RNA, and genetic data. Plurality of biomarkers 120 may include one or more markers including but not limited to antinuclear antibody levels, Rheumatoid factor, Sjogren's antibodies, Anti-Tubulin, Associated with alcoholic liver disease, demyelinating disease, Grave's disease, Hashimoto's thyroiditis, infectious agent exposure PANDAS/ANDAS/OCD, rheumatoid arthritis, and recent onset type 1 diabetes, Anti-Myelin basic protein, Related to the risk for multiple sclerosis, autism, PANDAS/ANDAS/OCD, and systemic lupus erythematosus (SLE), Anti-Myelin oligodendrocyte glycoprotein (MOG), Found in various demyelinating diseases, including multiple sclerosis, neuromyelitis optica spectrum disorders (NMOSD), idiopathic optic neuritis (ON), acute disseminated encephalomyelitis (ADEM), multiphasic disseminated encephalomyelitis (MDEM), Devic's disease, and tumefactive demyelinating disease, Anti-Myelin proteolipid protein, A useful marker in patients with seronegative anti-myelin basic protein, the frequent marker in active multiple sclerosis and optic neuritis, Anti-Neurofascin, Found mainly in combined central and peripheral demyelination (CCPD), a rare demyelinating condition affecting both CNS and peripheral nervous system (PNS) tissues, and also in chronic inflammatory demyelinating polyneuropathy (CIDP) and axonal injury in patients with multiple sclerosis (MS), Anti-MAG, Anti-MAG peripheral neuropathy is a very rare disease caused by anti-MAG antibodies that destroy MAG protein leading to disruptions of normal myelin production and healthy peripheral nerve activity.

With continued reference to FIG. 1, plurality of biomarkers 120 may include one or more markers of blood brain barrier disruption, including but not limited to Anti-s100b, Blood brain barrier integrity breach and sub-concussive episodes lead to the production of this antibody. Extravasated s100B may trigger a pathologic autoimmune reaction linking systemic and CNS immune responses, Anti-Glial fibrillary acidic protein, Anti-GFAP is produced when the protein enters the bloodstream after a rupture of the blood brain barrier, thus serves as a blood based diagnostic marker of brain injury, Anti-Microglia, Indicate a destruction of the blood brain barrier and are found to play a role in tissue destruction of Alzheimer's disease, Anti-Glucose regulated protein 78, Glucose-regulated protein 78-targeted antibodies could instigate blood brain barrier breakdown and development of hallmark anti-aquaporin-4 autoantibody pathology.

With continued reference to FIG. 1, plurality of biomarkers 120 may include one or more markers of optical and/or autonomic nervous system disorders including but not limited to Anti-Neuron specific enolase, Antibodies against neuron specific enolase are found in patients with optical neuropathies, Anti-Aquaporin 4, AQP4 IgG is involved in the development of neuromyelitis optica and revolutionized the understanding of the disease. Anti-Aquaporin4 antibodies have also been shown in patients with peripheral demyelination, Anti-Recoverin, One of the key components of antibody disorders of the CNS. They have also been shown to be associated with retinopathy which is characterized by impaired vision and photosensitivity, Anti-CV2, Seen in autoimmune paraneoplastic autonomic neuropathy and mixed axonal and demyelinating peripheral neuropathy and the like.

With continued reference to FIG. 1, plurality of biomarkers 120 may include one or more markers of peripheral neuropathy, including but not limited to Anti-GM1, Associated with multi-focal motor neuropathy and lower motor neuropathy, characterized by muscle weakness and atrophy, Anti-GM2, A potential peripheral nerve antigen for neuropathy-associated autoantibodies, Anti-Hu, The most frequent manifestation of sensory neuropathy with frequent autonomic involvement, Anti-Ri, Can be detected in patients with the paraneoplastic opsoclonus/myoclonus syndrome. Neoplasms most often associated with anti-Ri include breast cancer, gynecological cancers, and small cell lung cancer, Anti-Amphiphysin, Often found in the serum of patients with stiff-person syndrome and the like.

With continued reference to FIG. 1, plurality of biomarkers 120 may include one or more markers of neuromuscular disorders, including but not limited to Anti-Acetylcholine receptors, Found in myasthenia gravis disease which destroys the receptor function, leading to a neuromuscular transmission defect, which then causes hypofunction, fatigue, and inflammation of skeletal muscles and produces serum antibodies against muscle antigens, Anti-Muscle specific kinase, An important marker in patients without anti-acetylcholine receptor antibodies in myasthenia gravis disease, Anti-Voltage gated calcium channels, Responsible for Lambert-Eaton myasthenic syndrome (LEMS), a rare autoimmune disorder of the neuromuscular junction, Anti-Voltage gated potassium channels, Downregulate the potassium channels expressed on the peripheral nerve terminal leading to nerve hyperexcitability, Anti-Titin, Present in 70-90% of thymoma autoimmune myasthenia gravis (MG) patients, and in approximately 50% of late-onset acetylcholine-MG patients without thymoma and the like.

With continued reference to FIG. 1, plurality of biomarkers 120 may include one or more markers of brain autoimmunity, including but not limited to Anti-Purkinje cell, Autoimmunity to a class of GABAergic neurons located in the cerebellum, which can produce abnormalities and decline in gross motor functions, Anti-Yo, Suggest that a patient with neurologic symptoms has a paraneoplastic syndrome. In addition, their presence also often suggests the nature of the underlying tumor, Anti-Amyloid beta (25-35), Levels of autoantibodies reacting with oligomers of the short, neurotoxic fragment Aβ (25-35) are significantly higher in AD patients than in healthy controls, Anti-Amyloid beta (1-42), A signature marker in Alzheimer's disease, Anti-RAGE peptide, Found in Alzheimer's disease patients, and particularly higher in AD patients with diabetes, Anti-Tau, Found in the neurofibrillary tangles in brains of individuals who have Alzheimer's disease, Anti-Glutamate, Found in epilepsy, encephalitis, cerebellar ataxia, systemic lupus erythematosus (SLE) and neuropsychiatric SLE, Sjogren's syndrome, schizophrenia, mania or stroke, Anti-Dopamine, Associated with movement disorders characterized by parkinsonism, dystonia, and Sydenham chorea, Anti-Hydroxytryptamine, Found mainly in autoimmune encephalitis, Anti-Alpha-synuclein, Mainly elevated in Parkinson's disease and Alzheimer's disease, Anti-α1 and β2 adrenergic receptors, Found mainly in patients with different dementia forms such as unclassified, Lewy body, vascular, and Alzheimer's dementia, Anti-Endothelin A receptor, Found in vascular dementia and the like.

With continued reference to FIG. 1, plurality of biomarkers 120 may include one or more markers of brain inflammation, including but not limited to Anti-NMDA receptor, Found in anti-NMDA receptor encephalitis, Anti-AMPA receptor, May play a role in Alzheimer's disease, ATN classification, cerebrospinal fluid B-amyloid, hyperphosphorylated Tau, hippocampal volume, characterized by decreased AMPA activation and synapse loss, Anti-Dopamine receptors, Associated with Parkinson's disease and other disorders of low dopamine status, Anti-GABA receptors, Associated with temporal lobe epilepsy (TLE), Parkinson's disease (PD) and Huntington's disease (HD) and other neurodegenerative disorders that involve disruptions in gamma-amino butyric acid (GABA) signaling, Anti-Dipeptidyl aminopeptidase-like protein 6, Associated with encephalitis, Anti-Glycine receptor, Helpful in the diagnosis of patients with symptoms and signs that include ocular motor and other brainstem dysfunction, hyperekplexia, stiffness, rigidity, myoclonus and spasms, Anti-Neurexin 3, Associated with a severe but potentially treatable encephalitis in which the antibodies cause a decrease of neurexin-3a and alter synapse development, Anti-Contactin-associated protein-like 2, Diseases associated with CNTNAP2 include Pitt-Hopkins-Like Syndrome 1 and Autism 15, Anti-Leucine-rich glioma-inactivated protein 1, LGI1 antibody—associated encephalitis has increasingly been recognized as a primary autoimmune disorder, Anti-Ma, Present in men with testicular tumors and isolated or combined limbic encephalitis (LE), diencephalic encephalitis (DE), or brainstem encephalitis (BE) and the like.

With continued reference to FIG. 1, plurality of biomarkers 120 may include one or more markers of infection, including but not limited to Anti-HSV-1, HSV-1 has been reported to have a pathogenesis role in Herpes simplex encephalitis (HSE) and seropositivity to HSV-1 antibodies has been correlated with increased risk of Alzheimer's disease, Anti-HSV-2, Herpes simplex encephalitis (HSE) is a disorder commonly associated with HSV-2. HSE due to HSV-2 may occur without meningitis features. Antibodies against HSV-2 have shown positive correlation in patients with symptoms of HSE, Anti-EBV, Antibodies against the EBV nuclear antigen complex (EBNAc) and EBNA-1 have been correlated with increased risk of multiple sclerosis (MS), Anti-CMV, Cytomegalovirus (CMV) infections have been reported frequently to be associated with Guillain-Barre syndrome (GBS). There is a potential for molecular mimicry between GM2 and antigens induced by CMV infection, Anti-HHV-6, Human herpesvirus-6 (HHV-6) is frequently associated with neurologic diseases, including multiple sclerosis (MS), epilepsy, encephalitis, and febrile illness, Anti-HHV-7, HHV-7 has been less frequently associated with CNS disease than HHV-6, but found to be associated with encephalitis, meningitis, and demyelinating conditions. Similar to HHV 6A, increased levels of HHV-7 were found in multiple brain regions in Alzheimer's disease (AD) patients, Anti-Streptococcal A, Anti-streptococcal A antibodies are shown to cross react with different brain proteins that could lead to neuropsychiatric symptoms including PANDAS characterized by pediatric obsessive-compulsive disorder and the like.

With continued reference to FIG. 1, plurality of biomarkers 120 may include one or markers including but not limited to aluminum, mercury, lead, cadmium, or arsenic levels. Plurality of biomarkers 120 may include arsenic levels. Plurality of biomarkers 120 may include levels of fibrinogen, plasma cystatin C, and/or brain natriuretic peptide—please include Neuron specific enolase (NSE), Glial fibrillary acidic protein (GFAP), Amyloid beta, Abeta 1-42, Abeta 1-40, Abeta42/Abeta40 ratio, Total Tau, s100b, Neurofilament light, alpha synuclein, Brain-derived neurotrophic factor (BDNF) and the like.

Continuing to refer to FIG. 1, plurality of biomarkers 120 may include measures of lung function such as forced expiratory volume, one second (FEV-1) which measures how much air can be exhaled in one second following a deep inhalation, forced vital capacity (FVC), which measures the volume of air that may be contained in the lungs. User input may include a measurement blood pressure, including without limitation systolic and diastolic blood pressure. User input may include a measure of waist circumference. Plurality of biomarkers 120 may include body mass index (BMI) or measurements of Intracellular and Extracellular Water, Phase Angle, Body composition, lean body mass, fat mass, All measured via Bioimpedence Analysis. User input may include one or more measures of bone mass and/or density such as dual-energy x-ray absorptiometry. Plurality of biomarkers 120 may include one or more measures of muscle mass. Plurality of biomarkers 120 may include one or more measures of physical capability such as without limitation measures of grip strength, evaluations of standing balance, evaluations of gait speed, pegboard tests, timed up and go tests, and/or chair rising tests.

With continued reference to FIG. 1, plurality of biomarkers 120 may include, without limitation any result of any medical test and/or physiological assessments, or the like. For instance, user input may include any medical tests and/or results used to diagnose a renal disorder, such as a glomerular filtration rate test ("GFR"). "GFR," as used in this disclosure, is a urine test to check for albumin. Albumin is a protein that can pass into the urine when the kidneys are damaged.

Still referring to FIG. 1, plurality of biomarkers 120 may include other cardiovascular data such as heart rate data, blood pressure data, or the like, for instance captured using audio and/or oximetry devices. User input may include respiratory data such as audio capture of pulmonary sounds using a microphone or the like. Plurality of biomarkers 120 may include neurological data. Plurality of biomarkers 120 may include digestive audio data. Plurality of biomarkers 120 may include visual data captured regarding one or more elements of externally visible patient anatomy. Plurality of biomarkers 120 may capture one or more elements of human subject bodily motion, including gait, posture or gestural motions. In an embodiment, plurality of biomarkers 120 may include glycocalyx-related biomarkers, as explained above. In an embodiment, plurality of biomarkers 120 may include any marker of autoantibodies, toxicity, inflammation, cellular senescence, autophagy, mitochondrial function, neurodegeneration and the like.

Continuing to refer to FIG. 1, physiological data 116 may be received through user input 112. In this disclosure, a "user input" is a piece of data received from a user, possibility through a remote user input device. "User input device" may include without limitation, a display in communication with computing device 104, where a display may include any display as described herein. User input device may include an additional computing device, such as a mobile device, laptop, desktop, computer, and the like. In an embodiment, user input device may have a touch screen to interact with the user. User may input physiological data 116 through user input device. physiological data 116 may be extracted from a user input 112 once user submits it to the computing device 104. Any of physiological data 116 may be input via user inputs 112 at user input device, and/or retrieved from database 108. Additionally, user input device may use a remote sensor to obtain physiological data 116. A "remote sensor," as used in this disclosure, is a device that captures data of human subject and transmits that data to computing device 104, either by transmitting the data to user input device which relays the data to computing device 104, or by transmitting the data separately over a network connection. Physiological data 116 may be transmitted via communication channel interface and/or via a separate network connection formed, for instance, using a secure sockets layer (SSL) and/or hypertext transfer protocol-secure (HTTPS) process. Remote sensor may include, without limitation, a camera such as a digital camera incorporated in a mobile device or the like, a microphone such as a mobile device microphone, a motion sensor, which may include one or more accelerometers, gyroscopes, magnetometer, or the like. Remote sensor may include one or more peripheral devices such as a peripheral pulse oximeter or the like. Remote sensor may include a network-connected device such as a network connected digital scale or the like. In an embodiment, remote sensor may be used to capture audio or visual data concerning one or more portions of human subject's anatomy. For instance, and without limitation, a microphone may be pressed against one or more portions of human subject at direction of user over communication channel, causing capture of audio data from the one or more portion of human subject; as a non-limiting example, audio data of human subject lungs, heart, digestive system, or the like may be so captured. As a further example, user may instruct human subject to train a camera on one or more portions of anatomy to capture visual data concerning such one or more portions. Such physiological data may be combined; for instance, audio capture of circulatory system noise data may be combined with pulse oximetry data from a peripheral pulse oximeter and/or motion-sensor data indicating a degree of activity. Remote sensor may include an electrical sensor such as a portable electrocardiogram device or the like. Generally, any sensor capable of capturing data of human subject and transmitting such data locally or over a network may be used as a remote sensor.

Plurality of biomarkers 120 may comprise at least a glycocalyx degradation biomarker. In this disclosure, a "glycocalyx degradation biomarker" is a biomarker that indicates abnormalities found as a result of any study that analyzes the glycocalyx of a user. In this disclosure, "glycocalyx" is a highly hydrated fibrous meshwork of carbohydrates that covers the membrane of cells. Glycocalyx and its degradation is further explained herein with reference to FIG. 3.

At least a glycocalyx degradation biomarker may relate to a health condition treatable with a plasma exchange treatment. As used in this specification, a "plasma exchange treatment" is defined as a treatment performed by removing plasma from the body and the replacing the plasma with plasma replacement therapy treatment. Also, as used herein, a "plasma replacement therapy treatment" is a method of treatment that differs from the plasma exchange treatment but gives the same effects and/or results. "Plasma," as used in this disclosure, is the liquid portion of blood. Health conditions suitable for plasma exchange treatment may include, but not limited to, treatment of neurological conditions such as Guillain-Barre Syndrome, chronic inflammatory demyelinating polyneuropathy, and the like. Nonneurologic conditions such as Myasthenia Gravis, hyperviscosity syndrome, thrombotic thrombocytopenic purpura, hemolytic uremic syndrome, idiopathic thrombocytopenia, and the like, may be suitable for plasma exchange treatment. Other conditions may include, but not limited to, transplant rejection of solid organs such as the kidneys and heart, multiple sclerosis, and the like.

Computing device 104 may measure glycocalyx degradation biomarker to predict the patient's response to plasma exchange treatment. Measurement may include circulating levels of endothelial growth factor A and D (VEGF-A, VEGF-D), angiopoietin-1 (Angpt-1), Von Willebrand factor-cleaving protease (ADAMTS13), soluble angiopoietin-1 receptor (soluble TIE2), tissue factor (TF), soluble thrombomodulin (TM), shed ectodomain of angiotensin-converting enzyme 2 receptor (ACE2), and tumor necrosis factor-alpha (TNF-α). Computing device 104 may also measure changes in capillary density in a pooled density of capillaries between 4-6 microns.

Still referring to FIG. 1, at least a glycocalyx degradation biomarker may include a plurality of capillary density measurements. As defined in this disclosure, "capillary density" refers to a length of red cell-perfused capillaries per observation area (cm-1). For instance, capillary density refers to the number of capillaries present at a certain site in the human body. Measuring capillary density may provide information that may help diagnose a user with a potential disease. For instance, loss of capillary density, and thus flow of blood through tissues, may be considered a feature of aging. Such loss of blood flow may provide an indication that a user may be at risk for, for example, heart disease. In another non-limiting example, loss of capillary density may be associated with connective tissue diseases ("CTD"). "CTD," as used in this disclosure, are a diverse group of rheumatologic disorders characterized by the presence of autoantibodies and systemic organ involvement, frequently including the lung or chest. An experimental setup may include, but not limited to a side stream dark field ("SDF") camera (CapiScope HVCS, KK Technology, Honiton, UK). was used to visualize the sublingual microvasculature. The dynamic lateral movement of red blood cells ("RBCs") is measured which provides an indication as to the capillary density. The plurality of capillary density measurements are measured using sublingual video microscopy. In this case, the camera, such as the SDF camera, is positioned towards the sublingual mucosa and maneuvered until a clear image of the microcirculation is acquired. As an example, the camera may use green light emitting stroboscopic diodes (540 nm) to detect the hemoglobin of passing red blood cells (RBCs). With the use of, for example, a 5× objective with a 0.2 numerical aperture, images are captured, providing a 325-fold magnification in 720×576 pixels at 23 frames per second. Each complete measurement may consist of, at least ten 2-second videos (40 frames/video), containing a total of about 3000 vascular segments of 10 μm length each. All videos are deliberately obtained from different positions to counterbalance spatial heterogeneity of the sublingual microcirculation.

Additionally or alternatively, with continued reference to FIG. 1, physiological data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological data 116 may include, without limitation, immune function data such as Interleukine-6 (IL-6), TNF-alpha, systemic inflammatory cytokines, and the like.

Continuing to refer to FIG. 1, physiological data 116 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological data 116 may include measures of glucose metabolism such as fasting glucose levels and/or hemoglobin A1-C (HbA1c) levels. Physiological data 116 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological data 116 may include measures of estimated glomerular filtration rate (eGFR). Physiological data 116 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological data 116 may include antinuclear antibody levels. Physiological data 116 may include aluminum levels. Physiological data 116 may include arsenic levels. Physiological data 116 may include levels of fibrinogen, plasma cystatin C, and/or brain natriuretic peptide.

Continuing to refer to FIG. 1, physiological data 116 may include measures of lung function such as forced expiratory volume, one second (FEV-1) which measures how much air can be exhaled in one second following a deep inhalation, forced vital capacity (FVC), which measures the volume of air that may be contained in the lungs. Physiological data 116 may include a measurement blood pressure, including without limitation systolic and diastolic blood pressure. Physiological data 116 may include a measure of waist circumference. Physiological data 116 may include body mass index (BMI). Physiological data 116 may include one or more measures of bone mass and/or density such as dual-energy x-ray absorptiometry. Physiological data 116 may include one or more measures of muscle mass. Physiological data 116 may include one or more measures of physical capability such as without limitation measures of grip strength, evaluations of standing balance, evaluations of gait speed, pegboard tests, timed up and go tests, and/or chair rising tests.

With continued reference to FIG. 1, physiological data 116 may include, without limitation any result of any medical test and/or physiological assessments, or the like. For instance, physiological data 116 may include any medical tests and/or results used to diagnose a renal disorder, such as a glomerular filtration rate test ("GFR"). "GFR," as used in this disclosure, is a urine test to check for albumin. Albumin is a protein that can pass into the urine when the kidneys are damaged.

Still referring to FIG. 1, physiological data 116 may include other cardiovascular data such as heart rate data, blood pressure data, or the like, for instance captured using audio and/or oximetry devices. Physiological data 116 may include respiratory data such as audio capture of pulmonary sounds using a microphone or the like. Physiological data 116 may include neurological data. Physiological data 116 may include digestive audio data. Physiological data 116 may include visual data captured regarding one or more elements of externally visible patient anatomy. Physiological data 116 may capture one or more elements of human subject bodily motion, including gait, posture or gestural motions. In an embodiment, physiological data 116 may include glycocalyx-related biomarkers, as explained above.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Continuing to refer to FIG. 1, computing device 104 is also configured to determine a concentration 124 for each biomarker of the plurality of biomarkers 120. As used in this disclosure, a "concentration" is a numerical measure of the presence, quantity, ratio to volumes of tissue, fluid, or the like, or other measure of prevalence of a particular marker. A kidney disorder, for example, may be indicated by changes in concentration 124 within a particular range of neutrophil gelatinase-associated lipocalin (NGAL). A concentration 124 within a suitable range for a marker may, for example, indicate the absence of a particular health condition. A concentration 124 outside the suitable range may indicate, for example, the presence of a particular health condition. A value considered outside the suitable range may indicate a value that is higher or lower than a value included within the suitable range. A concentration 124 may be a value published in, for example, a research journal. Alternatively, a concentration may be determined by experimentation. For example, an analysis of a renal disorder may include a control experiment to determine the values of a particular concentration that fall within the suitable range. After the control experiment, a urine sample, for instance, may be analyzed and a measurement for a particular concentration 124 made and compared to the value of the control sample. A patient may be suffering from a renal disorder if, for example, the value of a particular concentration 124 falls outside the suitable range of values of the concentration for the control experiment. A value for the concentration 124 that is higher or lower than the suitable range may result in a positive result for a renal disorder.

Still referring to FIG. 1, computing device 104 is also configured to classify each biomarker to a disease condition 136 and a treatment label 140 as a function of the concentration 124 and a treatment classifier 128. In an embodiment, treatment classifier 128 is generated by receiving treatment training data 132 correlating markers related to glycocalyx degradation and concentrations for each marker indicative of glycocalyx degradation with a disease condition 136 and a treatment label 140. As used in this disclosure, a "disease condition" is an abnormal state of health that interferes with the usual, healthy activities or feelings of the user. For example, symptoms such as, but not limited to, decreased urination, nausea, shortness of breath, and the like, may be indicative of a disease condition 136 called "acute renal failure." A disease condition may include but is not limited to a neurological disease such as Guillain-Barre syndrome, chronic inflammatory demyelinating polyneuropathy, myasthenia gravis, polyneuropathy associated with paraproteinemia, pediatric autoimmune neuropsychiatric disorders associated with streptococcal infection (PANDAS), Lambert-Eaton myasthenic syndrome, multiple sclerosis, chronic focal encephalitis, neuromyelitis optica and the like. A disease condition may include a hematologic disease such as thrombotic thrombocytopenic purpura, atypical hemolytic uremic syndrome, hyper viscosity syndrome, cryoglobulinemia, ABO-incompatible haemopoietic stem cell transplantation, pure red cell aplasia, atypical hemolytic uremic syndrome, myeloma with cast nephropathy, red cell alloimmunization and the like. A disease condition may include a renal disease such as Goodpasture's syndrome, antineutrophil cytoplasmic antibody (ANCA), recurrent focal segmental glomerular sclerosis, antibody-mediated rental transplant rejection and the like. A disease condition may include a metabolic disease such as metabolic syndrome, familiar hypercholesterolemia, Wilson's disease, Refsum's disease and the like. A disease condition may include an immunological condition such as catastrophic antiphospholipid syndrome, systemic lupus erythematosus (SLE), COVID-19, autoimmune conditions and the like.

"Training data," as used herein, is data containing correlations that a machine-learning process may use to model relationships between two or more categories of data elements. Treatment training data 132 may be received and/or collected from experts or from users that may have may have been diagnosed with a health condition with particular disease markers where plasma exchange treatment improved and/or cure the health condition. Treatment training data 132 may be received as a function of determinations of a health condition based on disease markers, health condition metrics, and/or measurable values. Treatment training data 132 set may be received and/or otherwise developed during one or more past iterations of the previous treatment training data vectors. Treatment training data 132 may be received from one or more remote devices that at least correlate a marker related to glycocalyx degradation and concentration to a treatment label 140, where a remote device is an external device to computing device 104. or instance, and without limitation, training data may include a plurality of data entries, each entry representing a set of data elements that were recorded, received, and/or generated together; data elements may be correlated by shared existence in a given data entry, by proximity in a given data entry, or the like.

Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in treatment training data 132 according to various correlations; correlations may indicate causative and/or predictive links between categories of data elements, which may be modeled as relationships such as mathematical relationships by machine learning processes as described in further detail below. Treatment training data 132 may be formatted and/or organized by categories of data elements, for instance by associating data elements with one or more descriptors corresponding to categories of data elements. As a non-limiting example, treatment training data 132 may include data entered in standardized forms by persons or processes, such that entry of a given data element in a given field in a form may be mapped to one or more descriptors of categories. Elements in treatment training data 132 may be linked to descriptors of categories by tags, tokens, or other data elements; for instance, and without limitation, treatment training data 132 may be provided in fixed-length formats, formats linking positions of data to categories such as comma-separated value (CSV) formats and/or self-describing formats such as extensible markup language (XML), enabling processes or devices to detect categories of data.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \geq P(B)$, where $P(A B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Alternatively or additionally, and with continued reference to FIG. 1, treatment training data 132 may include one or more elements that are not categorized; that is, treatment training data 132 may not be formatted or contain descriptors for some elements of data. Machine learning algorithms and/or other processes may sort treatment training data 132 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same treatment training data 132 to be made applicable for two or more distinct machine learning algorithms as described in further detail below. Treatment training data 132 used by computing device 104 may correlate any input data as described in this disclosure to any output data as described in this disclosure. Training data may contain entries, each of which correlates a machine learning process input to a machine learning process output, for instance without limitation, one or more elements of biomarker data to a taste index. Training data may be obtained from previous iterations of machine-learning processes, user inputs, and/or expert inputs. Computing device 104 may train treatment classifier 128 using treatment training data 132. As used in this disclosure, a "treatment label" is data indicating possible treatment to alleviate the disease condition. A treatment label may specify a treatment frequency. A "treatment frequency," as used in this disclosure, is a recommendation as to a particular quantity of treatments that may be prescribed for a user. A quantity of treatments may include but is not limited to a number of treatments, a time frame for a treatment, a dose of a treatment, a time frame for a treatment, a number of repetitions of a treatment and the like. For instance and without limitation, a quantity of treatments may recommend that a user is to receive 3 plasma treatments, with each of the 3 plasma treatments occurring once every two weeks for a total duration of six weeks. In yet another non-limiting example, a quantity of treatments may recommend that a user is to receive a treatment once per day for a total of three consecutive days. For example, a decrease in the concentration of ADAMTS13, an antithrombotic metalloprotease which cleaves highly adhesive large von Willebrand factor (VWF) which may indicate a degraded glycocalyx, may be tagged with a label indicating that the possibility of treatment using plasma replacement therapy, such as, but not limited to "Plasma Treatment Candidate." Additionally, treatment label may further include information denoting which type of treatments may be useful in curing a degradation of the user's glycocalyx. Using treatment training data 132, computing device 104 trains treatment classifier 128. Furthermore, treatment classifier 128 may include multiple classifiers, such as a disease classifier and a treatment label classifier. Disease classifier may identify the disease condition while the treatment label classifier may identify a treatment or treatment label. Training data for a disease classifier may include any information used to correlate the user to a disease condition, including physiological data. Training data for a treatment label classifier may include any information used to correlate the user to a treatment label or treatment. Training data may be obtained from previous iterations of machine-learning processes, user inputs such as physiological data, and/or expert inputs from medical professionals. A description on machine learning and the use of classifiers follows below.

Continuing in reference to FIG. 1, treatment training data 132 may train a treatment machine-learning model. Treatment machine-learning model may include any machine-learning algorithm (such as K-nearest neighbors algorithm, a lazy naïve Bayes algorithm, and the like), machine-learning process (such as supervised machine-learning, unsupervised machine-learning), or method (such as neural nets, deep learning, and the like), as described in further detail below. Treatment machine-learning model may be trained to derive an algorithm, function, series of equations, or any mathematical operation, relationship, or heuristic, that can automatedly accept an input and assign a numerical value to, or otherwise calculate an output. Treatment machine-learning model may derive individual functions describing unique relationships observed from the training data for each biomarker, wherein different relationships may emerge between users and user cohorts. Treatment machine-learning model inputs treatment training data explained below and outputs a disease condition 136 and a treatment label 140.

Continuing in reference to FIG. 1, training data for classifying each biomarker to a disease condition 136 and a treatment label 140 may include results from biomarker samples, health state questionnaires regarding symptomology, medical histories, physician assessments, lab work, and the like. Treatment training data may originate from the subject, for instance via a questionnaire and a user interface with computing device 104 to provide medical history data. Receiving treatment training data may include receiving whole genome sequencing, gene expression patterns, and the like, for instance as provided by a genomic sequencing entity, hospital, database, the Internet, and the like. Treatment training data may include raw data values recorded and transmitted to computing device 104 via a wearable device such as a pedometer, gyrometer, accelerometer, motion tracking device, bioimpedance device, ECG/EKG/EEG monitor, physiological sensors, blood pressure monitor, blood sugar and volatile organic compound (VOC) monitor, and the like. Treatment training data may originate from an individual other than user, including for instance a physician, lab technician, nurse, caretaker, psychologist, therapist, and the like. Treatment training data may be input into computing device 104 via a graphical user interface for instance for a health state questionnaire for onboarding of user symptomology. It is important to note that training data for machine-learning processes, algorithms, and/or models used herein may originate from any source described for immune profile training data. Training data and machine learning process are further explained below with reference to FIG. 5.

Using treatment classifier 128, computing device 104 classifies each biomarker and concentration 124 to a disease condition 136 and treatment label 140. The use of classifiers may be implemented, without limitation, as described earlier in this disclosure. As a non-limiting example, in sepsis, the degraded glycocalyx layer becomes thinner and sparser, allowing plasma proteins, such as albumin, to move across a blood vessel, leading to tissue edema formation. This degradation releases glycocalyx components, such as syndecan-1, heparan sulfate, hyaluronan, chondroitin sulfates, and the like into the plasma. Based on inputs such as the biomarkers and the elevated concentrations, treatment classifier 128 may output a classification of a disease condition such as sepsis and a label such as "Plasma Treatment Candidate."

Additionally, computing device 104 may utilize the plurality of capillary density measurements, as explained earlier, to receive health density training data. In this disclosure, "health density training data" is training data correlating information included in physiological data 116 and/or treatment labels to various densities in blood vessels such as without limitation glycocalyx degradation capillary density measurements, historical glycocalyx degradation capillary density measurements, or the like. For example, health density training data may include measurements correlating to capillary density. Computing device 104 may also be configured to retrieve historical glycocalyx degradation capillary density measurements from database 108. The capillary density measurements and the historical measurements are used as input training data and are used to train a health density classifier similarly to how the treatment classifier is trained earlier. Health density classifier than outputs a treatment label and/or disease condition as a result of being trained by the health density training data. A machine-learning model and/or classifier may be used to associate each aspect of any of the data described herein relation to the capillary density measurements, such as the capillary density measurements or health density training data, with treatments and/or diseases. Machine learning model and classifier may be any of the classifiers or machine-learning models described herein.

Health density training data may be received and/or collected from experts or from users that may have may have had a procedure to measure the capillary density by, for example, sublingual video microscopy. Health density training data may be received as a function of determinations of a health condition based on disease markers, health condition metrics, and/or measurable values. Health density training data set may be received and/or otherwise developed during one or more past iterations of the previous health density training data vectors. Health density training data may be received from one or more remote devices that correlate capillary density measurements and historical capillary density measurements related to glycocalyx degradation to a treatment label where a remote device is an external device to computing device 104, and without limitation, health density training data may include a plurality of data entries, each entry representing a set of data elements that were recorded, received, and/or generated together; data elements may be correlated by shared existence in a given data entry, by proximity in a given data entry, or the like. Health density training data may be obtained from previous iterations of machine-learning processes, user inputs such as physiological data, and/or expert inputs from medical professionals. Using the health density training data, computing device trains the health density classifier. Computing device 104 is configured to classify the capillary density measurements to a treatment label.

Continuing to refer to FIG. 1, computing device 104 is also configured to generate a treatment plan 144 as a function of disease condition 136 and the treatment label 140. As used in this disclosure, a "treatment plan" is a set of instructions for treating at least one disease condition. A treatment plan 144 may include a list of medicaments to treat a disease condition, a procedure to treat a disease condition, a supplement to treat a disease condition and the like. A treatment plan may include specific instructions for administration of such medicaments. These instructions may include, but are not limited to, the specific time period to take the medicaments, method of administration, such as orally, topically, or rectally, specific restrictions on food and/or beverages while under the care of treatment plan 144, supplements that may help the condition, supplements that may be averse to the condition, and the like. A "disease condition," as used in this disclosure, is any disorder of structure or function identified in a human being and/or animal. For instance and without limitation, a disease condition may include but is not limited to A disease condition may include a predisposition to be at risk of developing a disorder in the future. For example, a disease condition may identify that a user has a predisposition to develop Type 2 Diabetes Mellitus as a result of an elevated fasting blood glucose measurement. A "procedure," as used in this disclosure, is a course of action intended to achieve a result in the delivery of healthcare. A procedure may include but is not limited to a surgery, prescribing a particular course of action, a plasma exchange, an imaging test, a medical intervention and the like. For instance and without limitation, a procedure may include the stimulation of stem cells to induce multi-tissue regeneration within a user's body. In yet another non-limiting example, a procedure may include an open incisional hernia repair. Treatment plan 144 may include contact information about the prescriber and/or professional responsible for managing treatment plan 144. Contact information may include, but not limited to, the prescriber's name, contact phone number, emergency contact number, and a secondary contact number for another professional in case the prescriber is not available. In an embodiment, treatment plan 144 may include a plasma exchange treatment. The plasma exchange treatment may be implemented in treatment plan 144, without any limitations, as described earlier in this disclosure. Treatment plan 144 may include information detailing amount, timing, frequency and/or dosing of one or more instructions for treating at least one disease condition. For instance and without limitation, treatment plan 144 may instruct a patient with a disease condition such as cardiovascular disease to receive six months of plasma therapy with a unique composition of ingredients to be include in the plasma therapy and for the plasma therapy to be delivered to the patient one day per month for each of the six months. In an embodiment, treatment plan 144 may include instructions for a user to follow prior to and immediately after a procedure. For example, a treatment plan 144 may detail that a user should consume a supplement containing 500 mg of quercetin once per day for 3 days prior to administration of plasma therapy.

With continued reference to FIG. 1, in another embodiment computing device 104 is configured to receive treatment frequency training data. Treatment frequency training data correlates health conditions and frequency of treatment to time period required to improve the health condition. The use of training data has been described earlier in this disclosure. Treatment frequency training data may be received and/or collected from experts or from users that may have may have received at least one treatment or a plurality of treatments and have shown improvement for a particular health disorder. Treatment frequency training data may be received as a function of determinations based on the frequency of treatment for a health condition, frequency of treatment metrics, and/or measurable values. Treatment frequency training data set may be received and/or otherwise developed during one or more past iterations of the previous treatment frequency training data vectors. Treatment frequency training data may be received from one or more remote devices that capillary density measurements and historical capillary density measurements related to glycocalyx degradation to a treatment label where a remote device is an external device to computing device 104. Without limitation, treatment frequency training data may include a plurality of data entries, each entry representing a set of data elements that were recorded, received, and/or generated together; data elements may be correlated by shared existence in a given data entry, by proximity in a given data entry, or the like. Treatment frequency training data may further correlate any physiological data and/or disease data to frequency of treatments, wherein frequency refers to the rate at which the treatments occur. Using the treatment frequency training data, computing device trains a machine-learning process using the treatment frequency training data. A treatment plan is outputted as a function of at least one health condition and the machine-learning process. For instance, a user may be diagnosed with diabetes. A treatment plan based on the onset of diabetes may include one plasma treatment weekly for 3 months. Alternatively, based on a second input which may include physiological data 116, the treatment plan may be changed to twice per week for an additional 3 months.

Figure 2:
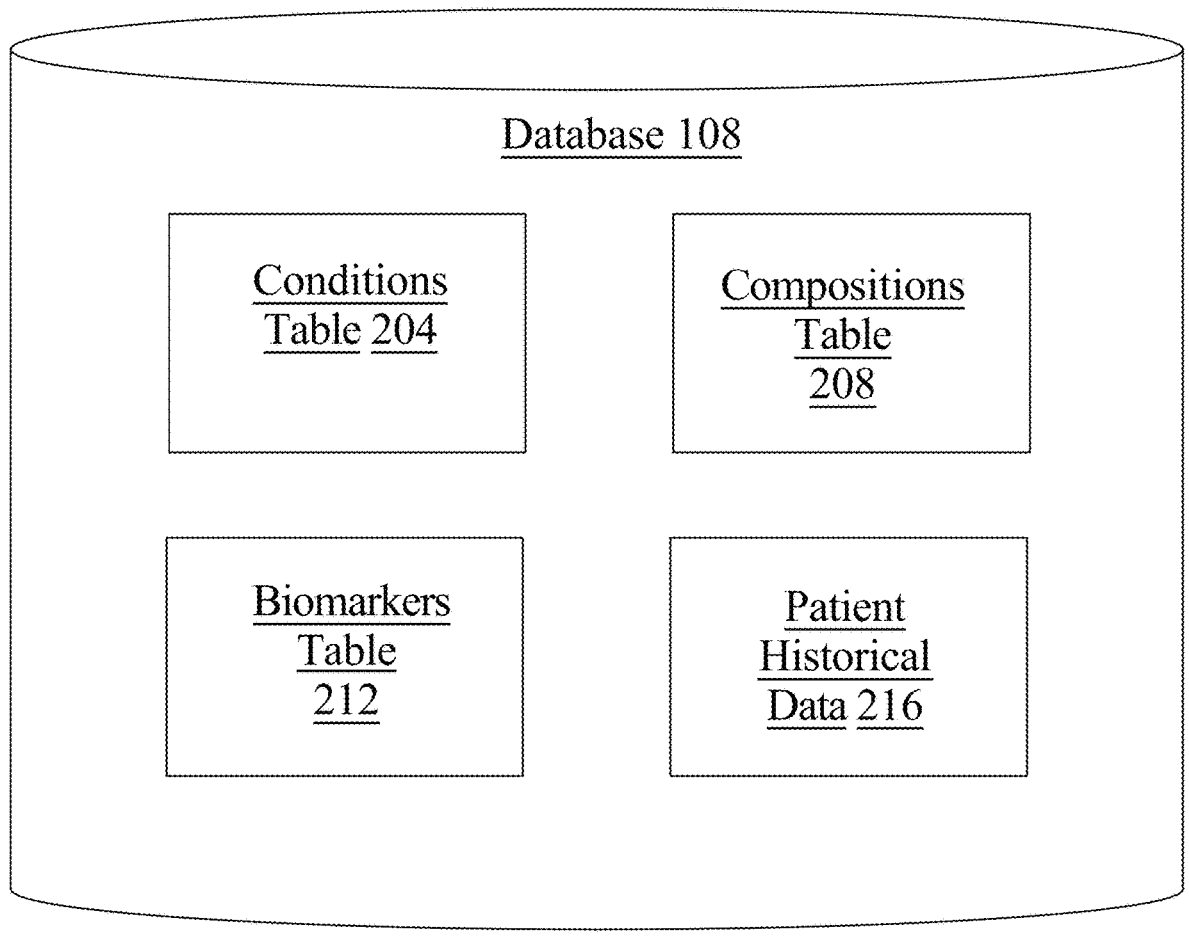
FIG. 2 is a block diagram of an exemplary embodiment of a database.

Now referring to FIG. 2, an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of a first condition, for instance as defined below; as a result, a query may be able to retrieve all rows from any table pertaining to a given first condition. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, a conditions table 204, which may be used to store records and attributes related to medical conditions. This may include, but not limited to, symptoms of the conditions, demographic of conditions, treatments, or the like. As another non-limiting example, one or more tables in database 108 may include a compositions table 208 which may be used to store regenerative treatment compositions used to treat medical conditions, frequency of administration of treatment, and the like. As another non-limiting example, one or more tables in database 108 may include a biomarkers table 212. A biomarkers table 212 may include, but not limited to correlations of biomarkers to conditions, values of biomarkers reflecting the presence of a condition, data on biomarker research, and the like. As another non-limiting example, one or more tables in database 108 may include a patient historical data table 216. A patient historical data table 216 may include data from prior regenerative treatments administered to patients, patient outcome based on the treatment, frequency of treatment received for a particular patient, and the like.

Figure 3:
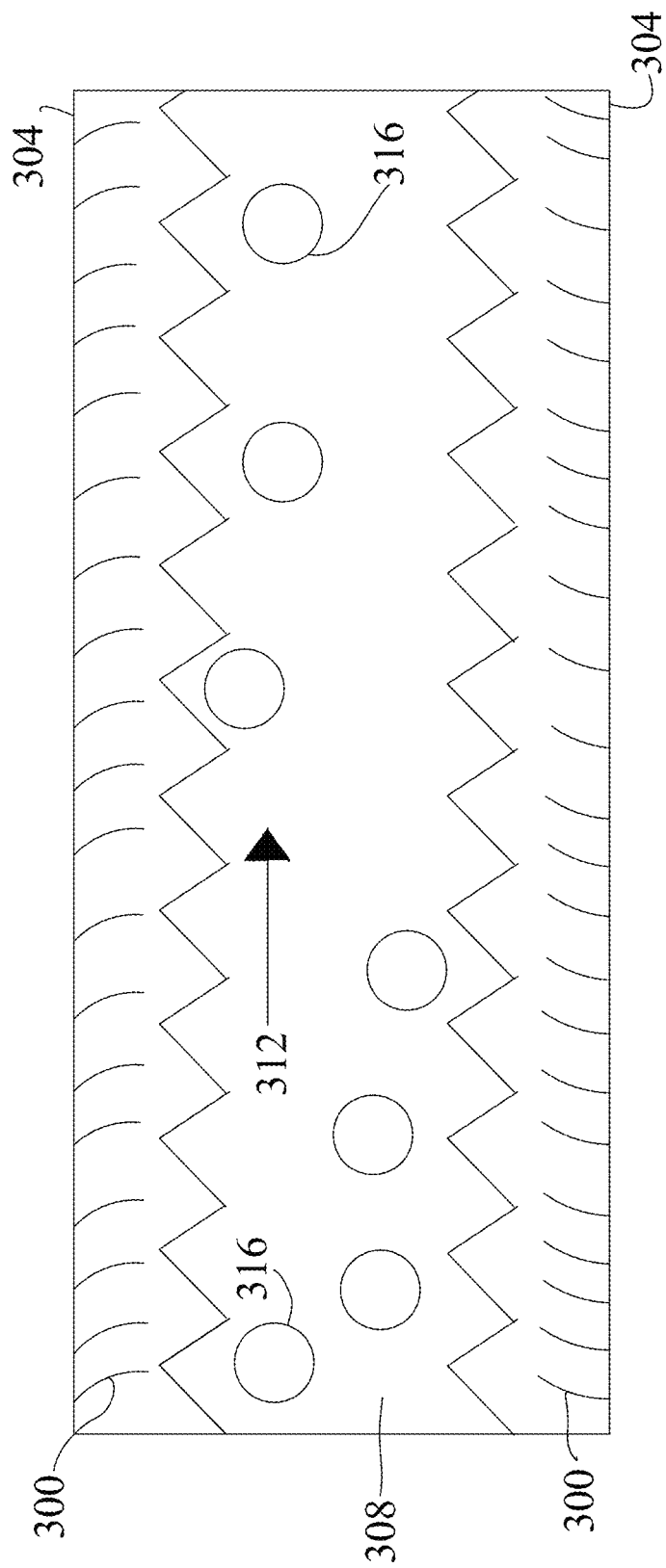
FIG. 3 is a block diagram of an exemplary embodiment of a vessel demonstrating the glycocalyx layer.

Now referring to FIG. 3, plurality of biomarkers 120 includes at least one biomarker from plurality of biomarkers 120 related to the degradation of glycocalyx 300. Degradation of glycocalyx 300 may be associated with disease states such as diabetes, chronic kidney disease (CKD), inflammatory conditions, sepsis, hypernatremia, hypervolemia and ischemia/reperfusion injury. In a non-limiting example, endothelium 304 represents a layer of flat cells that line the inside of vessel 308. In this disclosure, "endothelium" is the tissue which forms a single layer of cells lining various organs and cavities of the body, especially the blood vessels. A "vessel", as used herein, is a tubular structure carrying blood through the tissues and organs. The flat cells represented by endothelium produce glycocalyx 300 to protect vessel 308 from damage. Glycocalyx 300 is composed of heparin and chondroitin sulfate. In an embodiment, "heparin" is a compound that inhibits blood coagulation, while "chondroitin sulfate" is a chemical used for the building blocks of cartilage. Degradation of glycocalyx 300 may result in, for instance, exposure to rushing blood 312 and blood components 316 which are passing through vessel 308. Glycocalyx 300 may function to allow nutrients to pass or to stop certain substances from entering vessel 308. Since glycocalyx 300 includes heparin, a blood thinner, glycocalyx 300 may regulate blood coagulation by preventing blood from coagulating on the surface of vessel 308 as blood flows through vessel 308. Glycocalyx 300 may also regulate the entrance of immune cells that produce an immune response to an antigen. Glycocalyx 300 may stimulate endothelial nitric oxide (NO) release which assists in the dilation of vessel 308 with subsequent increase in blood flow through vessel 308. Examples of biomarkers related to the degradation of glycocalyx 300 include, but are not limited to, circulating levels of endothelial growth factor A and D (VEGF-A, VEGF-D), Angiopoietin-1 (Angpt-1), Von Willebrand factor-cleaving protease (ADAMTS13), soluble angiopoietin-1 receptor (soluble TIE2), tissue factor (TF), Soluble thrombomodulin (TM), shed ectodomain of angiotensin-converting enzyme 2 receptor (ACE2), tumor necrosis factor-alpha (TNF-α), and the like.

With continued reference to FIG. 3, in an embodiment, degradation of glycocalyx 300 may be measured based on a movement of red blood cells expressed as a perfused boundary region. As used in this disclosure, the "perfused boundary region" reflects the thickness of the endothelial glycocalyx, where loss of the integrity of the glycocalyx allows deeper penetration of the red blood cells into glycocalyx 300 covering endothelium 304. Higher perfused boundary region indicates thinner glycocalyx 300. For instance, in a non-limiting example, using sublingual video microscopy, the hemoglobin of passing red blood cells (RBCs) is captured, and the dynamic lateral RBC movement into the glycocalyx expressed as the perfused boundary region, in μm is calculated. A degraded glycocalyx allows more RBCs to penetrate deeply toward the endothelial surface, with a consequent increase in the PBR.

Figure 4:
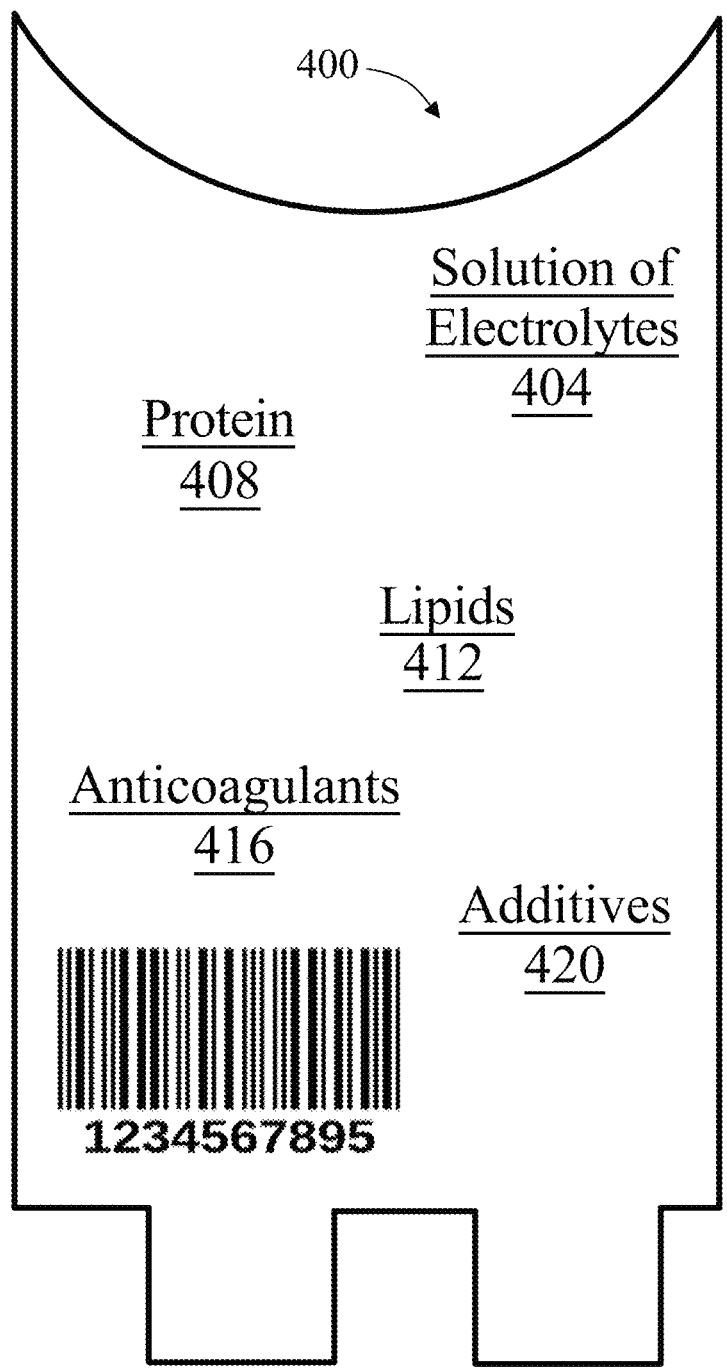
FIG. 4 is a block diagram of an exemplary embodiment of a replacement therapy treatment.

Now referring to FIG. 4, an exemplary replacement therapy treatment 400 that may be used in the plasma exchange treatment, as explained above, is disclosed. Replacement therapy treatment 400 may include solution of electrolytes 404. In this disclosure, "electrolytes" refer to a liquid configured to produce ions and help balance the amount of water in a patient's body. Solution of electrolytes 404 may include a mixture of sodium chloride, sodium lactate, potassium chloride, calcium chloride, and the like. Replacement therapy treatment 400 may include protein 408. In this disclosure, a "protein" is a complex substance that consists of amino acid residues joined by peptide bonds and do most of the work in cells required for the structure, function, and regulation of the body's tissues and organs.

The protein may include an albumin. Albumin may be present in an amount between about 30 g/L to about 60 g/L, between about 35 g/L to about 55 g/L, or between about 40 g/L to about 50 g/L. The composition of the replacement therapy treatment may include an amount of albumin at least about 60 g/L or at least about 55 g/L. Protein 408 may be globulins. A "globulin" is any of a group of simple proteins soluble in salt solutions and forming a large fraction of blood serum protein. Examples of globulins include, but not limited to immunoglobulin G (IgG), immunoglobulin M (IgM), immunoglobulin A (IgA), immunoglobulin D (IgD), immunoglobulin E (IgE), and the like. In a non-limiting example, the composition of the replacement therapy treatment may include intravenous immunoglobulin. Non-limiting examples of intravenous immunoglobulin may include, but not limited to immunoglobulin G1 (IgG1), immunoglobulin G2 (IgG2), immunoglobulin G3 (IgG3), immunoglobulin G4 (IgG4), or combinations thereof. A total amount of globulins may include an amount between about 30 g to about 50 g, between about 35 g to about 40 g, or between about 30 g to about 40 g. In an embodiment, one or more globulins may be infused to a patient in a particular order and/or at a specified dose. For example, a patient may receive 20 g of albumin infused. In yet another non-limiting example, a patient may receive an infusion of 20 g of albumin alternated with an infusion of 10 g IVIG 5%. In yet another non-limiting example, the composition of the replacement therapy treatment may include a number of globulins at least about 1 g/L to about 20 g/L. Protein 408 may include fibrinogen. Fibrinogen may be present in an amount between about 150 mg/dl to about 400 mg/dl, between about 250 mg/dl to about 300 mg/dl, or between about 350 mg/dl to about 400 mg/dl.

Additionally, and with continued reference to FIG. 4, the composition of replacement therapy treatment 400 may include lipid 412. A "lipid", as used herein, is any of various organic compounds that are insoluble in water, including fats, waxes, oils, hormones, and certain components of membranes and function as energy-storage molecules and chemical messengers. This may include, but not limited to, phospholipid fatty acid such as lysophosphatidylcholine, phosphatidylcholine, phosphatidylethanolamine, phosphatidylinositol, sphingomyelin and the like; fat-soluble vitamins (like vitamins A, D, E, K); a steroid, and the like. A phospholipid may be present in an amount between about 1.0 mg/m L to about 2.0 mg/ml, or between about 1.0 mg/ml to about 2.2, or between about 1.5 mg/ml to about 2.2.

Additionally or alternatively, and still with reference to FIG. 4, the composition for the replacement therapy treatment 400 may include anticoagulant 416. As used herein, an "anticoagulant" is a type of blood thinner used to reduce the ability of the blood to clot. Examples of anticoagulants 416 may include, but not limited to ethylenediaminetetraacetic acid (EDTA), sodium citrate, citrate dextrose, Heparin, Enoxaparin, Dalteparin, Nadroparin, aspirin, warfarin, and the like.

Additionally, or alternatively, and with continued reference to FIG. 4, the composition for replacement therapy treatment 400 may include additives 420. In this disclosure, "additives" are chemical substances added to foods to produce specific desirable effects. For example, additives 420 may include a surfactant, which is a compound that lowers the surface tension between two liquids, between a gas and a liquid, or between a liquid and a solid. Additives 420 may include a stabilizer. A "stabilizer" is a chemical that is used to prevent degradation. Examples of stabilizer include, but are not limited to, PVP (Povidone), PVA (Polyvinyl alcohol), PEG (Polyethylene glycol), HPMC (Hypromellose), HPC (Hydroxypropyl cellulose), HEC (Hydroxyethyl cellulose), NaCMC (Carboxymethylcellulose sodium), SD (Docusate sodium), SLS (Sodium lauryl sulfate), PEI (Polyethylene imine), TPGS (D-α-tocopheryl polyethylene glycol succinate), PEO (Polyethylene oxide) or PPO (Polypropylene oxide), and combinations thereof.

With continued reference to FIG. 4, the composition for replacement therapy treatment 400 may include one or more vitamins, minerals, and/or additional ingredients. "Vitamins" are, as used herein, organic molecule that is an essential micronutrient which an organism needs in small quantities for the proper functioning of its metabolism. "Minerals", herein, are chemical element required as an essential nutrient by organisms to perform functions necessary for life. This may include but is not limited to any vitamin, mineral, alpha lipoic acid, NADH, glutathione, exosomes, ions, resveratrol, Coenzyme Q10, ubiquinol, 1-arginine.

With continued reference to FIG. 4, replacement therapy treatment may include a series of one or more ingredients given to a user at the same time and/or in a sequence of treatments given our a specified period of time. For example, replacement therapy may include a single infusion containing two ingredients given to a user in the course of one treatment. In yet another non-limiting example, a replacement therapy may include a series of infusions containing a multiple of ingredients, with each ingredient given in a particular series of steps and at a particular period of time within the treatment. In an embodiment, replacement therapy treatment may be delivered to a user with any delivery mechanism including but not limited to oral delivery, intravenous delivery, subcutaneous delivery, intranasal delivery, rectal delivery, vaginal delivery, dermal delivery and the like. In an embodiment, replacement therapy treatment may include one or more additional therapies given before, during, and/or after delivery of replacement therapy treatment. An "additional therapy," as used in this disclosure, is any therapy given in addition to replacement therapy treatment. An additional therapy may include but is not limited to a prescription medication, supplement, food, exercise program, over the counter medication, a homeopathic remedy, a natural medicine, an herbal extract and the like. For example, a user may be prescribed an oral supplement such as bromelain 400 mg to be taken twice daily for 3 days prior to receiving a replacement therapy treatment.

With continued reference to FIG. 4, the composition for replacement therapy treatment 400 may include one or more additional ingredients. An "additional ingredient" as used in this disclosure may include a supplemental ingredient added to replacement therapy treatment 400. An additional ingredient may include but is not limited to a protein, amino acid, organic acid, bioidentical compound, biosimilar compound, a hormone, a cell-signaling molecule, RNA, DNA, antisense RNA, and/or any other pharmaceutical and/or non-pharmaceutical ingredient.

With continued reference to FIG. 4, the composition for the replacement therapy treatment replacement therapy may include stem cells. A "stem cell" as used in this specification, is a cell that has the ability to develop into a specialized cell and replace cells or tissue that has been damaged. Stem cells may be adult stem cells. "Adult stem cells" as used in this disclosure are stem cells obtained for certain regions of the adult body such as, but not limited to, the epidermis of the skin, the lining of the small intestine, the bone marrow, and the like. Stem cells may be pluripotent. A "pluripotent stem cell" as used in this disclosure, is a stem cell that has the ability to undergo self-renewal and to give rise to all cells of the tissues in the body. A stem cell may include an exosome. An "exosome," as used in this disclosure, is an extracellular vesicle produced in an endosomal compartment of a eukaryotic cell. A stem cell may include a very small embryonic like stem cell (VSEL). In an embodiment, a stem cell may be produced and/or generated using 3-D printing technology. Composition for replacement treatment may include a determination of a volume of plasma to be removed from a user to make way for a replacement therapy. This may be determined based on one or more factors including but not limited to a user's height, weight, body composition, hemoglobin, fibrinogen, and/or one or more additional factors.

Figure 5:
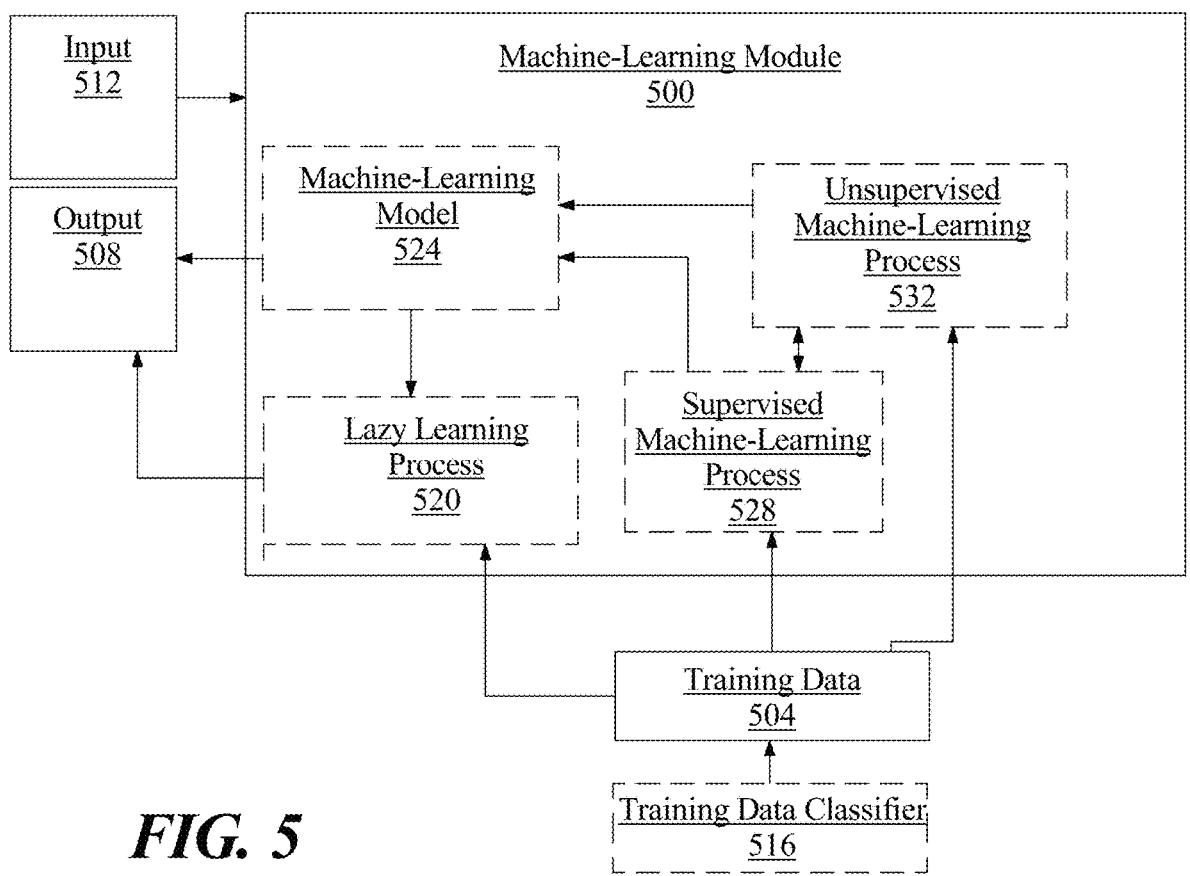
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, biomarkers indicative of glycocalyx degradation may serve as inputs, outputting other potential health disorders that a may use the same disease biomarkers.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a process whereby a computing device and/or any module and/or component operating thereon derives a classifier from training data 504. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to classify biomarkers indicative of glycocalyx degradation into categories such as, for example, a target organ, and the like.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning model 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a disease biomarker such as TNF-α and a concentration outside a suitable range, renal disorder as an outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 5, a "classifier," as used in this disclosure, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a process whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 5, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 5, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 5, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\Sigma_{i=0}^{n}a_{i}^{2}}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Figure 6:
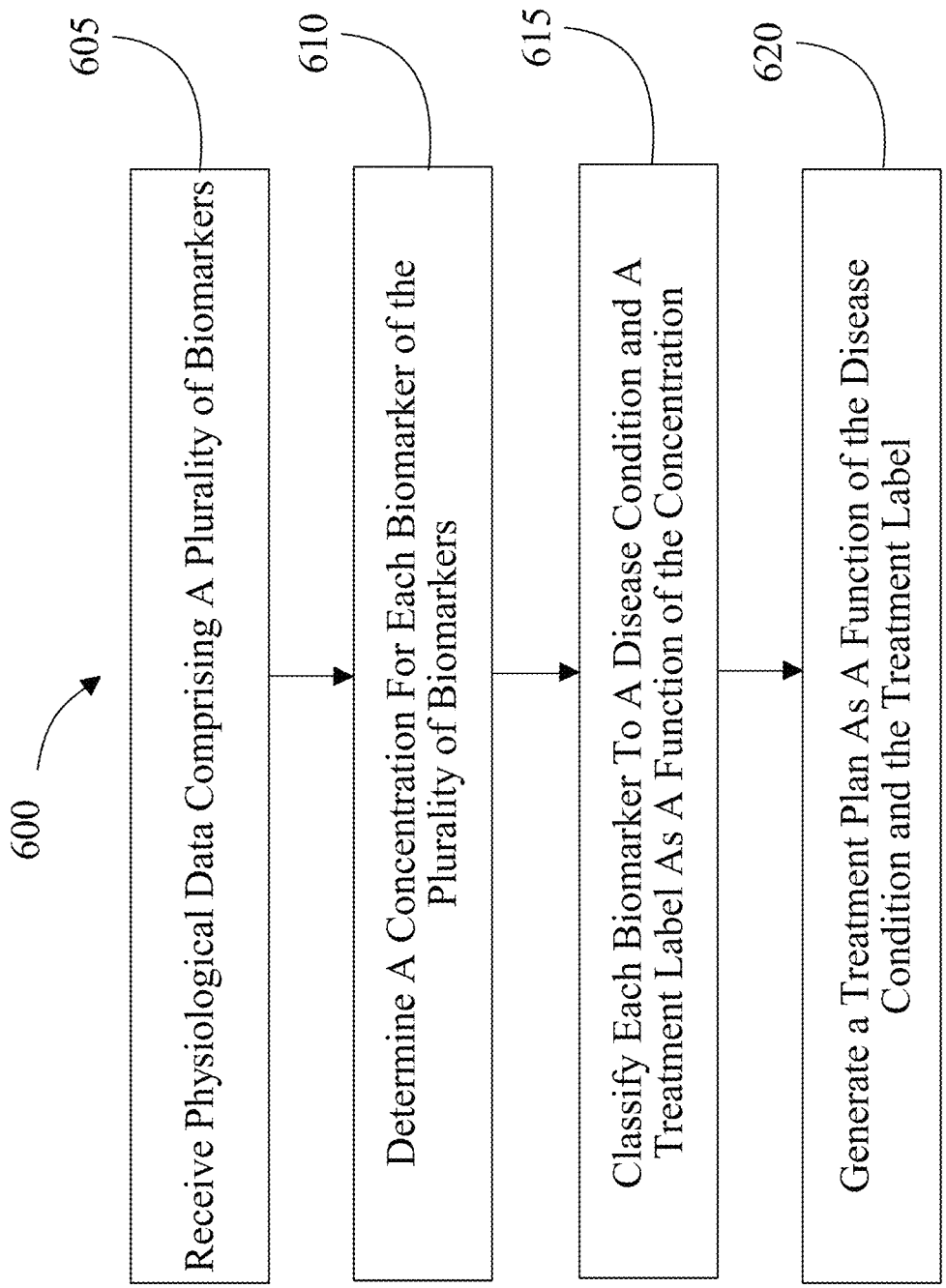
FIG. 6 is a flow diagram illustrating an exemplary embodiment of a method of generating a treatment plan for salutogenesis.

Now referring to FIG. 6, a flow diagram illustrating an exemplary embodiment of a method of generating a treatment plan for salutogenesis is presented. A treatment plan may be any of the plans described herein with reference to FIGS. 1 and 4.

Still referring to FIG. 6, at step 605, method 600 includes receiving physiological data 116 associated with a user and comprising a plurality of biomarkers 120. Plurality of biomarkers may include at least a glycocalyx degradation biomarker. At least a glycocalyx degradation biomarker may be measured as a function of a movement of red blood cells expressed as a perfused boundary region. At least a glycocalyx degradation biomarker relates to a health condition treatable with a plasma exchange treatment. In an embodiment, a health condition treatable with a plasma exchange treatment may include identification of a regenerative goal for the plasma exchange treatment. A "regenerative goal," as used in this disclosure, is any desired and/or intended outcome for a plasma exchange treatment. For example, a regenerative goal may be to improve a user's short-term memory. In yet another non-limiting example, a regenerative goal may be to improve a user's vision and to reduce the number of days each week that the user experiences symptoms of blurry vision. At least a glycocalyx degradation biomarker comprises a predictive marker. Physiological data 116 may include a plurality of capillary density measurements. Plurality of capillary density measurements may be measured using sublingual video microscopy. Physiological data 116 may include any of the data described herein with reference to FIGS. 1 and 2. Plurality of biomarkers 120 may include any of the biomarkers as described herein with reference to FIGS. 1 and 2.

Still referring to FIG. 6, at step 610, method 600 includes determining a concentration 124 for each biomarker of the plurality of biomarkers 120. Concentration 124 may include any of the concentrations as described herein with reference to FIG. 1.

Still referring to FIG. 6, at step 615, method 600 includes classifying each biomarker to a disease condition 136 and a treatment label 140 as a function of the concentration 124. Glycocalyx degradation biomarker may include any of the biomarkers described herein with reference to FIG. 1. Disease condition 136 may include any of the disease conditions as described herein with reference to FIG. 1. Treatment label 140 may include any of the treatment labels as described herein with reference to FIG. 1. Concentration 124 may include any of the concentrations as described herein with reference to FIG. 1.

Still referring to FIG. 6, method 600 may include receiving treatment training data 132 correlating each biomarker and its concentration 124 with disease condition 136 and the treatment label 140. Treatment training data may be any of the training data described herein with reference to FIGS. 1 and 5. Glycocalyx degradation biomarker may include any of the biomarkers described herein with reference to FIG. 1. Concentration 124 may include any of the concentrations as described herein with reference to FIG. 1. Disease condition 136 may include any of the disease conditions as described herein with reference to FIG. 1. Treatment label 140 may include any of the treatment labels as described herein with reference to FIG. 1.

Still referring to FIG. 6, method 600 may include training a treatment classifier 128 using the treatment training data 132. Computing device 104 may also receive health density training data correlating capillary density measurements and historical glycocalyx degradation capillary density measurements to the treatment label and trains a health density classifier using the health density training data. Treatment classifier may be any of the training classifiers described herein with reference to FIG. 1. Treatment training data may be any of the training data described herein with reference to FIGS. 1 and 5.

Still referring to FIG. 6, method 600 may further include classifying the at least a glycocalyx degradation biomarker to the disease condition and the treatment label using the treatment classifier. Glycocalyx degradation biomarker may include any of the biomarkers described herein with reference to FIG. 1. Disease condition 136 may include any of the disease conditions as described herein with reference to FIG. 1. Treatment classifier may be any of the training classifiers described herein with reference to FIG. 1.

Still referring to FIG. 6, at step 620, method 600 includes generating a treatment plan 144 as a function of the disease condition 136 and the treatment label 140. Treatment plan 144 includes plasma exchange. Computing device 104 is further configured to classify the capillary density measurements to the treatment label and generate the treatment plan as a function of the treatment label. Generating a treatment plan further comprises receiving treatment frequency training data, training a machine-learning process using the treatment frequency training data, and output the treatment plan as a function of at least one health condition and the machine-learning process. Treatment plan may be any of the treatment plans described herein with reference to FIGS. 1 and 4. Disease condition 136 may include any of the disease conditions as described herein with reference to FIG. 1. Treatment label 140 may include any of the treatment labels as described herein with reference to FIG. 1.

Still referring to FIG. 6, the method may use training data to train a machine-learning process to determine by comparing the dynamic natural movement of red blood cells, expressed as the perfused boundary region (PFB) of patients that have responded to plasma exchange against patients that have not responded to plasma exchange. Computing device may also generate a frequency of treatment based on training data correlating people responding to treatment to frequency of receiving a plasma treatment. Additionally, method 600 may employ looking information up in database 108 using the physiological data to determine if the human subject is a candidate for plasma exchange treatment; the response may indicate if the human subject may tolerate the plasma exchange treatment, how often the human subject should receive plasma exchange treatments, ingredients and/or nutrients that may be of benefit for the human subject to receive during the plasma treatments, and the like.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
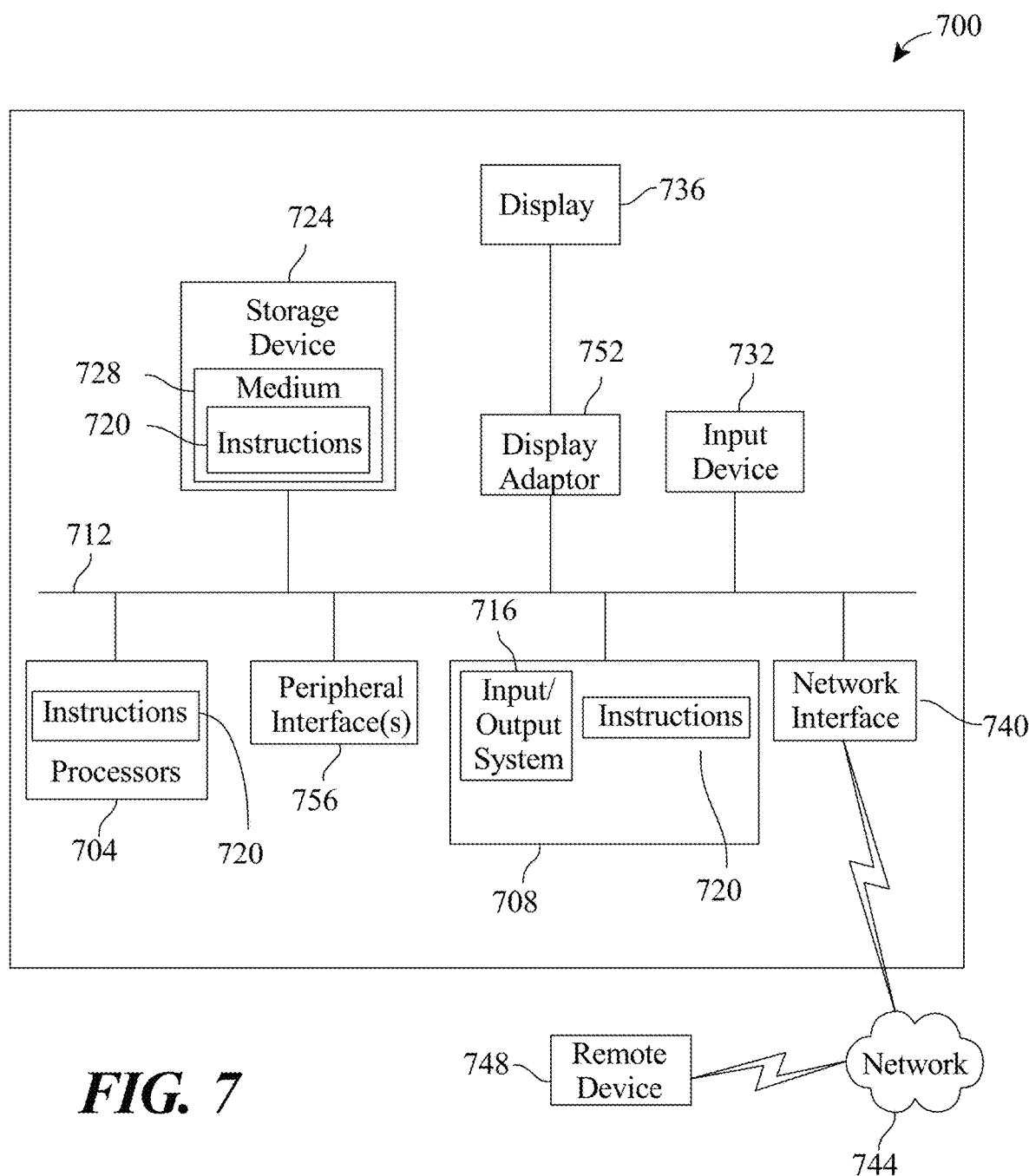
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems, according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generating a treatment plan for salutogenesis, the apparatus comprising:
   at least a processor; and
   a memory communicatively connected to the at least a processor, the memory containing instructions configuring the at least a processor to:
   receive physiological data associated with a user and comprising a plurality of biomarkers, wherein the plurality of biomarkers comprises at least a monitoring biomarker, a diagnostic biomarker, and a predictive biomarker, each biomarker being extracted from the user chemically;
   determine a concentration for each biomarker of the plurality of biomarkers;
   classify each biomarker of the plurality of biomarkers to a disease condition and a treatment label as a function of the concentration, wherein the classification further comprises:
      receiving treatment training data correlating each biomarker and its concentration with the disease condition and the treatment label;
      training, iteratively, a treatment classifier using the treatment training data, wherein the treatment training data further comprises data correlating biomarkers related to glycocalyx degradation; and
      classifying each biomarker to the disease condition and the treatment label using the treatment classifier, wherein the treatment classifier receives the plurality of biomarkers and the concentration for each biomarker as an input and outputs the disease condition and the treatment label; and
   generate a treatment plan as a function of the disease condition and the treatment label.

2. The apparatus of claim 1, wherein the plurality of biomarkers includes at least a glycocalyx degradation biomarker.

3. The apparatus of claim 2, wherein the at least a glycocalyx degradation biomarker is measured as a function of a movement of red blood cells expressed as a perfused boundary region.

4. The apparatus of claim 1, wherein the treatment plan includes plasma exchange.

5. The apparatus of claim 1, wherein physiological data includes a plurality of capillary density measurements.

6. The apparatus of claim 5, wherein the processor is further configured to:
   receive health density training data correlating capillary density measurements and historical glycocalyx degradation capillary density measurements to the treatment label; and
   train a health density classifier using the health density training data.

7. The apparatus of claim 5, wherein the processor is further configured to:
   classify the capillary density measurements to the treatment label; and
   generate the treatment plan as a function of the treatment label.

8. The apparatus of claim 5, wherein the plurality of capillary density measurements are measured using sublingual video microscopy.

9. The apparatus of claim 1, wherein generating the treatment plan further comprises:

receive treatment frequency training data, wherein the treatment frequency training data correlates health condition data and frequency of treatment data to time period required to improve the health condition;

train a machine-learning process using the treatment frequency training data; and output the treatment plan as a function of at least one health condition and the machine-learning process.

10. The apparatus of claim 1, wherein the treatment label identifies a treatment frequency.

11. A method for generating a treatment plan for salutogenesis, the method comprising:

receiving, at a processor, physiological data associated with a user and comprising a plurality of biomarkers, wherein the plurality of biomarkers comprises at least a monitoring biomarker, a diagnostic biomarker, and a predictive biomarker, each biomarker being extracted from the user chemically;

determining, at a processor, a concentration for each biomarker of the plurality of biomarkers;

classifying, at a processor, each biomarker of the plurality of biomarkers to a disease condition and a treatment label as a function of the concentration, wherein the classification further comprises:

receiving treatment training data correlating each biomarker and its concentration with the disease condition and the treatment label;

training, iteratively, a treatment classifier using the treatment training data, wherein the treatment training data further comprises data correlating biomarkers related to glycocalyx degradation; and classifying each biomarker to the disease condition and the treatment label using the treatment classifier, wherein the treatment classifier receives the plurality of biomarkers and the concentration for each biomarker as an input and outputs; and generating, at a processor, a treatment plan as a function of the disease condition and the treatment label.

12. The method of claim 11, wherein the plurality of biomarkers includes at least a glycocalyx degradation biomarker.

13. The method of claim 12, wherein the at least a glycocalyx degradation biomarker is measured as a function of a movement of red blood cells expressed as a perfused boundary region.

14. The method of claim 11, wherein the treatment plan includes plasma exchange.

15. The method of claim 11, wherein physiological data includes a plurality of capillary density measurements.

16. The method of claim 15, wherein the processor is further configured to:

receiving health density training data correlating capillary density measurements and historical glycocalyx degradation capillary density measurements to the treatment label; and training a health density classifier using the health density training data.

17. The method of claim 15, wherein the processor is further configured to:

classifying the capillary density measurements to the treatment label; and generating the treatment plan as a function of the treatment label.

18. The method of claim 15, wherein the plurality of capillary density measurements are measured using sublingual video microscopy.

19. The method of claim 11, wherein generating a treatment plan further comprises:

receiving treatment frequency training data, wherein the treatment frequency training data correlates health condition data and frequency of treatment data to time period required to improve the health condition;

training a machine-learning process using the treatment frequency training data; and outputting the treatment plan as a function of at least one health condition and the machine-learning process.

20. The method of claim 11, wherein generating the treatment label further comprises identifying a treatment frequency.

* * * * *